US006599230B2

(12) United States Patent
Hastings et al.

(10) Patent No.: US 6,599,230 B2
(45) Date of Patent: *Jul. 29, 2003

(54) INTRAVASCULAR RADIATION DELIVERY SYSTEM

(75) Inventors: Roger N. Hastings, Maple Grove, MN (US); Thomas R. Hektner, Medina, MN (US); Stewart M. Kume, Belmont, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 127 days.

This patent is subject to a terminal disclaimer.

(21) Appl. No.: 09/808,315

(22) Filed: Mar. 14, 2001

(65) Prior Publication Data

US 2001/0023308 A1 Sep. 20, 2001

Related U.S. Application Data

(63) Continuation of application No. 08/782,471, filed on Jan. 10, 1997, now Pat. No. 6,234,951, which is a continuation-in-part of application No. 08/608,655, filed on Feb. 29, 1996, now Pat. No. 5,882,290.

(51) Int. Cl.$^7$ .................................................. A61N 5/00
(52) U.S. Cl. ...................................... 600/3; 604/103.07
(58) Field of Search ......................... 600/1–8; 606/191, 606/194; 604/103.07, 103.08

(56) References Cited

U.S. PATENT DOCUMENTS

| 1,442,051 A | 1/1923 | Cummings |
| 2,546,761 A | 3/1951 | Loftus .......................... 128/1.2 |
| 2,862,108 A | 11/1958 | Meilink ........................ 250/106 |
| 2,955,208 A | 10/1960 | Stevens ........................ 250/108 |
| 3,060,924 A | 10/1962 | Rush ............................ 128/1.2 |
| 3,147,383 A | 9/1964 | Prest ............................ 250/108 |
| 3,324,847 A | 6/1967 | Zoumboulis ................. 128/1.2 |
| 3,505,991 A | 4/1970 | Hellerstein et al. ........... 128/1.1 |
| 3,643,096 A | 2/1972 | Jeffries, Jr. et al. ...... 250/108 R |
| 3,669,093 A | 6/1972 | Sauerwein et al. .......... 128/1.1 |
| 3,674,006 A | 7/1972 | Holmer .......................... 600/7 |
| 3,750,653 A | 8/1973 | Simon .......................... 128/1.2 |

(List continued on next page.)

FOREIGN PATENT DOCUMENTS

| CA | 2166915 A | 8/1996 |
| DE | 9102312.2 | 8/1992 |
| DE | 195 26 680 A1 | 1/1997 |

(List continued on next page.)

OTHER PUBLICATIONS

Fackelmann, "Harbinger of a Heart Attack", *Science News*, vol. 151, Jun. 14, 1997, pp. 374–375.

(List continued on next page.)

*Primary Examiner*—John P. Lacyk
(74) *Attorney, Agent, or Firm*—Christensen O'Connor Johnson Kindness PLLC

(57) ABSTRACT

An intravascular radiation delivery system including a catheter, a radiation source disposed in an open-ended lumen in the catheter and a closed-ended sheath surrounding the radiation source so as to prevent blood and other fluids from coming into contact with the radiation source. Preferably, the open-ended lumen is centered in the balloon for uniform radiation delivery. The catheter may include a blood perfusion lumen under the balloon or around the balloon. The open-ended lumen in the catheter may have a reduced diameter adjacent the distal end of the catheter to prevent the radiation source from exiting the lumen. Methods of using the radiation delivery system are also disclosed.

An alternative method of delivering radiation to a treatment site inside the vasculature of a patient using a gas-filled balloon catheter and a radiation source disposed in the balloon catheter. The treatment site is exposed to radiation, preferably beta radiation, through the gas-filled balloon.

15 Claims, 8 Drawing Sheets

U.S. PATENT DOCUMENTS

| | | | |
|---|---|---|---|
| 3,811,426 A | 5/1974 | Culver et al. ................. | 128/1.2 |
| 3,861,380 A | 1/1975 | Chassagne et al. ........... | 128/1.2 |
| 3,866,050 A | 2/1975 | Whitfield ..................... | 250/497 |
| 3,927,325 A | 12/1975 | Hungate et al. ............. | 250/435 |
| 3,970,073 A | 7/1976 | Greene ........................ | 128/1.2 |
| 4,096,862 A | 6/1978 | DeLuca ........................ | 128/348 |
| 4,220,864 A | 9/1980 | Sauerwein et al. .......... | 250/497 |
| 4,225,790 A | 9/1980 | Parsons, Jr. et al. ......... | 250/497 |
| 4,244,357 A | 1/1981 | Morrison ..................... | 128/1.2 |
| 4,281,252 A | 7/1981 | Parsons, Jr. et al. ......... | 250/497 |
| 4,314,157 A | 2/1982 | Gaines ......................... | 250/497 |
| 4,364,376 A | 12/1982 | Bigham ....................... | 128/1.1 |
| 4,402,308 A | 9/1983 | Scott ............................ | 128/1.2 |
| 4,584,991 A | 4/1986 | Tokita et al. ................. | 128/1.1 |
| 4,588,395 A | 5/1986 | Lemelson ..................... | 604/59 |
| 4,631,415 A | 12/1986 | Sauerwein et al. ....... | 250/497.1 |
| 4,697,575 A | 10/1987 | Horowitz ..................... | 128/1.2 |
| 4,702,228 A | 10/1987 | Russell, Jr. et al. ........... | 128/1.2 |
| 4,706,652 A | 11/1987 | Horowitz ..................... | 128/1.2 |
| 4,763,642 A | 8/1988 | Horowitz ..................... | 128/1.2 |
| 4,763,671 A | 8/1988 | Goffinet ....................... | 128/786 |
| 4,782,834 A | 11/1988 | Maguire et al. ............. | 128/344 |
| 4,784,116 A | 11/1988 | Russell, Jr. et al. ........... | 128/1.2 |
| 4,815,449 A | 3/1989 | Horowitz ...................... | 600/7 |
| 4,819,618 A | 4/1989 | Liprie ............................ | 600/7 |
| 4,851,694 A | 7/1989 | Rague et al. ............. | 250/497.1 |
| 4,861,520 A | 8/1989 | van't Hooft et al. ........ | 252/644 |
| 4,881,937 A | 11/1989 | van't Hooft et al. ........... | 600/3 |
| 4,897,076 A | 1/1990 | Puthawala et al. ........... | 600/7 |
| 4,936,823 A | 6/1990 | Colvin et al. .................. | 600/7 |
| 4,963,128 A | 10/1990 | Daniel et al. .................. | 600/7 |
| 4,969,863 A | 11/1990 | van't Hooft et al. ........... | 600/3 |
| 4,976,266 A | 12/1990 | Huffman et al. ............. | 128/659 |
| 4,976,680 A | 12/1990 | Hayman et al. ................ | 600/7 |
| 4,976,690 A | 12/1990 | Solar et al. .................... | 604/96 |
| 4,994,013 A | 2/1991 | Suthanthiran et al. .......... | 600/8 |
| 5,030,194 A | 7/1991 | Van't Hooft .................... | 600/3 |
| 5,032,113 A | 7/1991 | Burns .......................... | 604/96 |
| 5,059,166 A | 10/1991 | Fischell et al. ................. | 600/3 |
| 5,084,001 A | 1/1992 | Van't Hooft et al. ........... | 600/3 |
| 5,084,002 A | 1/1992 | Liprie ............................ | 600/7 |
| 5,092,834 A | 3/1992 | Bradshaw et al. ............. | 600/3 |
| 5,103,395 A | 4/1992 | Spako et al. ............. | 364/413.26 |
| 5,106,360 A | 4/1992 | Ishiwara et al. ................ | 600/2 |
| 5,120,973 A | 6/1992 | Rohe et al. .............. | 250/497.1 |
| 5,139,473 A | 8/1992 | Bradshaw et al. ............. | 600/3 |
| 5,141,487 A | 8/1992 | Liprie ............................ | 600/7 |
| 5,147,282 A | 9/1992 | Kan ............................. | 600/1 |
| 5,163,896 A | 11/1992 | Suthanthiran et al. .......... | 600/8 |
| 5,176,617 A | 1/1993 | Fischell et al. ................. | 600/3 |
| 5,183,455 A | 2/1993 | Hayman et al. ................ | 600/7 |
| 5,199,939 A | 4/1993 | Dake et al. .................... | 600/3 |
| 5,213,561 A | 5/1993 | Weinstein et al. ............. | 600/3 |
| 5,267,960 A | 12/1993 | Hayman et al. ............. | 604/106 |
| 5,282,781 A | 2/1994 | Liprie ............................ | 600/3 |
| 5,302,168 A | 4/1994 | Hess .............................. | 600/3 |
| 5,344,383 A | 9/1994 | Liping .......................... | 600/3 |
| 5,354,257 A | 10/1994 | Roubin et al. .................. | 600/7 |
| 5,370,685 A | 12/1994 | Stevens ......................... | 623/2 |
| 5,391,139 A | 2/1995 | Edmundson ................... | 600/7 |
| 5,395,300 A | 3/1995 | Liprie ............................ | 600/3 |
| 5,405,309 A | 4/1995 | Carden, Jr. ..................... | 600/3 |
| 5,409,015 A | 4/1995 | Palermo ....................... | 128/772 |
| 5,411,466 A | 5/1995 | Hess ............................. | 600/3 |
| 5,425,720 A | 6/1995 | Rogalsky et al. ............ | 604/198 |
| 5,429,582 A | 7/1995 | Williams ....................... | 600/2 |
| 5,484,384 A | 1/1996 | Fearnot ......................... | 600/3 |
| 5,498,227 A | 3/1996 | Mawad ......................... | 600/3 |
| 5,503,613 A | 4/1996 | Weinberger ................... | 600/3 |
| 5,503,614 A | 4/1996 | Liprie ............................ | 600/7 |
| 5,532,122 A | 7/1996 | Drukier ......................... | 435/5 |
| 5,538,494 A | 7/1996 | Matsuda ........................ | 600/1 |
| 5,540,659 A | 7/1996 | Teirstein ...................... | 604/104 |
| 5,556,389 A | 9/1996 | Liprie ........................... | 604/264 |
| 5,575,749 A | 11/1996 | Liprie ............................ | 600/3 |
| 5,605,530 A | 2/1997 | Fischell et al. ................. | 600/3 |
| 5,611,767 A | 3/1997 | Williams ....................... | 600/2 |
| 5,616,114 A | 4/1997 | Thornton et al. .............. | 600/3 |
| 5,618,266 A | 4/1997 | Liprie ........................... | 604/21 |
| 5,624,372 A | 4/1997 | Liprie ............................ | 600/3 |
| 5,643,171 A | 7/1997 | Bradshaw et al. ............. | 600/1 |
| 5,649,924 A | 7/1997 | Everett et al. ................ | 606/15 |
| 5,653,683 A | 8/1997 | D'Andrea ..................... | 604/21 |
| 5,662,580 A | 9/1997 | Bradshaw et al. ............. | 600/3 |
| 5,674,177 A | 10/1997 | Hehrlein et al. ................ | 600/3 |
| 5,683,345 A | 11/1997 | Waksman et al. .............. | 600/3 |
| 5,688,220 A | 11/1997 | Verin et al. .................... | 600/1 |
| 5,707,332 A | 1/1998 | Weinberger ................... | 600/3 |
| 5,713,828 A | 2/1998 | Coniglione .................... | 600/7 |
| 5,720,717 A | 2/1998 | D'Andrea ..................... | 604/21 |
| 5,722,984 A | 3/1998 | Fischell et al. ............. | 606/198 |
| 5,728,042 A | 3/1998 | Schwager ...................... | 600/3 |
| 5,730,698 A | 3/1998 | Fischell et al. ................. | 600/3 |
| 5,782,740 A | 7/1998 | Schneiderman ............... | 600/1 |
| 5,782,742 A | 7/1998 | Crocker et al. ................ | 600/3 |
| 5,795,286 A | 8/1998 | Fischell et al. ................. | 600/3 |
| 5,800,333 A | 9/1998 | Liprie ............................ | 600/3 |
| 5,803,895 A | 9/1998 | Kronholz et al. .............. | 600/3 |
| 5,807,231 A | 9/1998 | Liprie ............................ | 600/3 |
| 5,816,259 A | 10/1998 | Rose ........................... | 128/898 |
| 5,816,999 A | 10/1998 | Bischoff et al. ................ | 600/3 |
| 5,820,553 A | 10/1998 | Hughes ....................... | 600/426 |
| 5,833,593 A | 11/1998 | Liprie ............................ | 600/3 |
| 5,840,008 A | 11/1998 | Klein et al. ..................... | 600/3 |
| 5,840,009 A | 11/1998 | Fischell et al. ................. | 600/3 |
| 5,840,064 A | 11/1998 | Liprie ........................... | 604/96 |
| 5,843,163 A | 12/1998 | Wall ............................. | 623/1 |
| 5,849,036 A | 12/1998 | Zarate .......................... | 623/1 |
| 5,851,171 A | 12/1998 | Gasson ......................... | 600/3 |
| 5,851,172 A | 12/1998 | Bueche et al. ................. | 600/7 |
| 5,855,546 A | 1/1999 | Hastings et al. ............... | 600/3 |
| 5,857,956 A | 1/1999 | Liprie ............................ | 600/7 |
| 5,863,284 A | 1/1999 | Klein ............................ | 600/3 |
| 5,863,285 A | 1/1999 | Coletti ........................... | 600/3 |
| 5,865,720 A | 2/1999 | Hastings et al. ............... | 600/3 |
| 5,871,436 A | 2/1999 | Eury ............................. | 600/3 |
| 5,871,437 A | 2/1999 | Alt ................................ | 600/3 |
| 5,873,811 A | 2/1999 | Wang et al. .................... | 600/5 |
| 5,879,282 A | 3/1999 | Fischell et al. ................. | 600/3 |
| 5,882,290 A | 3/1999 | Kume ........................... | 600/3 |
| 5,882,291 A | 3/1999 | Bradshaw et al. ............. | 600/3 |
| 5,891,091 A | 4/1999 | Teirstein ...................... | 604/104 |
| 5,897,573 A | 4/1999 | Rosenthal et al. .......... | 606/224 |
| 5,899,882 A | 5/1999 | Waksman et al. ............. | 604/96 |
| 5,906,573 A | 5/1999 | Aretz ............................. | 600/3 |
| 5,910,101 A | 6/1999 | Andrews et al. ............... | 600/3 |
| 5,910,102 A | 6/1999 | Hastings ....................... | 600/3 |
| 5,913,813 A | 6/1999 | Williams et al. ............... | 600/3 |
| 5,916,143 A | 6/1999 | Apple et al. ................... | 600/3 |
| 5,919,126 A | 7/1999 | Armini .......................... | 600/3 |
| 5,924,973 A | 7/1999 | Weinberger ................... | 600/3 |
| 5,924,974 A | 7/1999 | Loffler .......................... | 600/3 |
| 5,925,353 A | 7/1999 | Mosseri .................... | 424/178.1 |
| 5,938,582 A | 8/1999 | Ciamacco, Jr. et al. ........ | 600/3 |
| 5,947,889 A | 9/1999 | Hehrlein ........................ | 600/3 |
| 5,947,924 A | 9/1999 | Liprie ........................... | 604/96 |
| 5,947,958 A | 9/1999 | Woodard et al. ............. | 606/1.5 |
| 5,957,829 A | 9/1999 | Thornton ...................... | 600/3 |
| 5,961,439 A | 10/1999 | Chernomorsky et al. ....... | 600/4 |
| 5,967,966 A | 10/1999 | Kronholz et al. .............. | 600/3 |
| 5,971,909 A | 10/1999 | Bradshaw et al. ............. | 600/3 |

| | | | |
|---|---|---|---|
| 5,976,106 A | 11/1999 | Verin et al. ............... 604/96 |
| 5,997,462 A | 12/1999 | Loffler ..................... 600/3 |
| 5,997,463 A | 12/1999 | Cutrer ...................... 600/8 |
| 6,010,445 A | 1/2000 | Armini et al. ............. 600/3 |
| 6,013,019 A | 1/2000 | Fischell et al. ........... 600/3 |
| 6,013,020 A | 1/2000 | Meloul et al. ............. 600/7 |
| 6,019,718 A | 2/2000 | Hektner .................... 600/3 |
| 6,024,690 A | 2/2000 | Lee et al. .................. 600/3 |
| 6,030,333 A | 2/2000 | Sioshansi et al. ......... 600/3 |
| 6,033,357 A | 3/2000 | Ciezki et al. .............. 600/3 |
| 6,048,300 A | 4/2000 | Thornton et al. ......... 600/7 |
| 6,050,930 A | 4/2000 | Teirstein ................... 600/3 |
| 6,053,858 A | 4/2000 | Bueche et al. ............ 600/3 |
| 6,059,713 A | 5/2000 | Urick et al. ............... 600/3 |
| 6,059,752 A | 5/2000 | Segal ...................... 604/107 |
| 6,059,812 A | 5/2000 | Clerc et al. .............. 606/198 |
| 6,066,083 A | 5/2000 | Slater et al. ............... 600/8 |
| 6,068,611 A | 5/2000 | Loffler et al. ............ 604/101 |
| 6,071,227 A | 6/2000 | Popowski et al. ......... 600/3 |
| 6,074,338 A | 6/2000 | Popowski et al. ......... 600/3 |
| 6,077,213 A | 6/2000 | Ciezki et al. .............. 600/3 |
| 6,093,142 A | 7/2000 | Ciamacco, Jr. ............ 600/3 |
| 6,095,966 A | 8/2000 | Chornenky et al. ....... 600/3 |
| 6,099,499 A | 8/2000 | Ciamacco, Jr. .......... 604/103 |
| 6,117,064 A | 9/2000 | Apple et al. .............. 600/3 |
| 6,120,533 A | 9/2000 | Fischell ................. 623/1.11 |
| 6,132,358 A | 10/2000 | Glenn et al. .............. 600/3 |
| 6,132,423 A | 10/2000 | Aita et al. ................. 606/7 |
| 6,146,323 A | 11/2000 | Fischell .................... 600/3 |
| 6,159,139 A | 12/2000 | Chiu ........................ 600/3 |
| 6,159,140 A | 12/2000 | Loeffler et al. ............ 600/3 |
| 6,159,142 A | 12/2000 | Alt ........................... 600/3 |
| 6,159,143 A | 12/2000 | Lennox ..................... 600/4 |
| 6,176,821 B1 | 1/2001 | Crocker et al. ............ 600/3 |
| 6,179,789 B1 | 1/2001 | Tu et al. .................. 600/585 |
| 6,183,409 B1 | 2/2001 | Armini ..................... 600/3 |
| 6,183,410 B1 | 2/2001 | Jacobsen et al. .......... 600/3 |
| 6,187,037 B1 | 2/2001 | Satz ...................... 623/1.34 |
| 6,192,271 B1 | 2/2001 | Hayman ................... 604/21 |
| 6,196,963 B1 | 3/2001 | Williams .................. 600/3 |
| 6,196,964 B1 | 3/2001 | Loffler et al. ............. 600/7 |
| 6,196,996 B1 | 3/2001 | Teirstein ................. 604/104 |
| 6,210,312 B1 | 4/2001 | Nagy ........................ 600/3 |
| 6,210,313 B1 | 4/2001 | Eury ........................ 600/3 |
| 6,210,315 B1 | 4/2001 | Andrews et al. .......... 600/7 |
| 6,210,316 B1 | 4/2001 | Slater et al. ............... 600/8 |
| 6,231,494 B1 | 5/2001 | Verin et al. ............... 600/1 |
| 6,234,951 B1 | 5/2001 | Hastings ................... 600/3 |

FOREIGN PATENT DOCUMENTS

| | | | |
|---|---|---|---|
| DE | 197 54 870 A1 | 8/1998 |
| DE | 197 24 233 C1 | 12/1998 |
| DE | 197 07 727 | 7/1999 |
| DE | 197 58 234 | 7/1999 |
| DE | 198 25 563 | 12/1999 |
| DE | 198 25 999 | 12/1999 |
| DE | 198 26 000 | 12/1999 |
| DE | 198 29 444 | 1/2000 |
| DE | 198 29 447 | 1/2000 |
| EP | 0 152 124 | 8/1985 |
| EP | 0 158 630 | 10/1985 |
| EP | 0 433 011 A1 | 6/1991 |
| EP | 0 447 745 A2 | 9/1991 |
| EP | 0 466 681 A1 | 1/1992 |
| EP | 0 474 994 | 3/1992 |
| EP | 0 514 913 A2 | 11/1992 |
| EP | 0 633 041 A1 | 1/1995 |
| EP | 0 686 342 A1 | 12/1995 |
| EP | 0 688 580 A1 | 12/1995 |
| EP | 0 696 906 B1 | 2/1996 |
| EP | 0 749 764 A1 | 12/1996 |
| EP | 0 754 472 A2 | 1/1997 |
| EP | 0 754 473 A2 | 1/1997 |
| EP | 0 593 136 B1 | 3/1997 |
| EP | 0 778 051 A1 | 6/1997 |
| EP | 0 801 961 A2 | 10/1997 |
| EP | 0 810 004 | 12/1997 |
| EP | 0 813 894 A2 | 12/1997 |
| EP | 0 629 380 B1 | 7/1998 |
| EP | 0 865 803 | 9/1998 |
| EP | 0 904 798 | 3/1999 |
| EP | 0 904 799 | 3/1999 |
| JP | 10071210 | 3/1998 |
| JP | 2000014810 | 1/2000 |
| WO | WO 86/03124 | 6/1986 |
| WO | WO 92/00776 | 1/1992 |
| WO | WO 93/04735 | 3/1993 |
| WO | WO 94/25106 | 11/1994 |
| WO | WO 94/26205 | 11/1994 |
| WO | WO 95/07732 | 3/1995 |
| WO | WO 95/19807 | 7/1995 |
| WO | WO 96/06654 | 3/1996 |
| WO | WO 96/10436 | 4/1996 |
| WO | WO 96/13303 | 5/1996 |
| WO | WO 96/14898 | 5/1996 |
| WO | WO 96/17654 | 6/1996 |
| WO | WO 96/22121 | 7/1996 |
| WO | WO 96/29943 | 10/1996 |
| WO | WO 96/40352 | 12/1996 |
| WO | WO 97/07740 | 3/1997 |
| WO | WO 97/09937 | 3/1997 |
| WO | WO 97/17029 | 5/1997 |
| WO | WO 97/18012 | 5/1997 |
| WO | WO 97/19706 | 6/1997 |
| WO | WO 97/25102 | 7/1997 |
| WO | WO 97/25103 | 7/1997 |
| WO | WO 97/40889 | 11/1997 |
| WO | WO 98/01183 | 1/1998 |
| WO | WO 98/01184 | 1/1998 |
| WO | WO 98/01185 | 1/1998 |
| WO | WO 98/01186 | 1/1998 |
| WO | WO 98/11936 | 3/1998 |
| WO | WO 98/16151 | 4/1998 |
| WO | WO 98/20935 | 5/1998 |
| WO | WO 98/25674 | 6/1998 |
| WO | WO 98/29049 | 7/1998 |
| WO | WO 98/30273 | 7/1998 |
| WO | WO 98/34681 | 8/1998 |
| WO | WO 98/36788 | 8/1998 |
| WO | WO 98/36790 | 8/1998 |
| WO | WO 98/36796 | 8/1998 |
| WO | WO 98/39052 | 9/1998 |
| WO | WO 98/39062 | 9/1998 |
| WO | WO 98/39063 | 9/1998 |
| WO | WO 98/40032 | 9/1998 |
| WO | WO 98/46309 | 10/1998 |
| WO | WO 98/55179 | 12/1998 |
| WO | WO 98/57706 | 12/1998 |
| WO | WO 99/01179 | 1/1999 |
| WO | WO 99/02219 | 1/1999 |
| WO | WO 99/04706 | 2/1999 |
| WO | WO 99/04856 | 2/1999 |
| WO | WO 99/10045 | 3/1999 |
| WO | WO 99/21615 | 5/1999 |
| WO | WO 99/21616 | 5/1999 |
| WO | WO 99/22774 | 5/1999 |
| WO | WO 99/22775 | 5/1999 |
| WO | WO 99/22812 | 5/1999 |
| WO | WO 99/22815 | 5/1999 |
| WO | WO 99/24116 | 5/1999 |
| WO | WO 99/24117 | 5/1999 |
| WO | WO 99/29354 | 6/1999 |

| | | |
|---|---|---|
| WO | WO 99/29370 | 6/1999 |
| WO | WO 99/29371 | 6/1999 |
| WO | WO 99/30779 | 6/1999 |
| WO | WO 99/34969 | 7/1999 |
| WO | WO 99/36121 | 7/1999 |
| WO | WO 99/39628 | 8/1999 |
| WO | WO 99/40962 | 8/1999 |
| WO | WO 99/40970 | 8/1999 |
| WO | WO 99/40971 | 8/1999 |
| WO | WO 99/40972 | 8/1999 |
| WO | WO 99/40973 | 8/1999 |
| WO | WO 99/40974 | 8/1999 |
| WO | WO 99/42162 | 8/1999 |
| WO | WO 99/42163 | 8/1999 |
| WO | WO 99/42177 | 8/1999 |
| WO | WO 99/44686 | 9/1999 |
| WO | WO 99/44687 | 9/1999 |
| WO | WO 99/49935 | 10/1999 |
| WO | WO 99/56825 | 11/1999 |
| WO | WO 99/56828 | 11/1999 |
| WO | WO 99/61107 | 12/1999 |
| WO | WO 99/62598 | 12/1999 |
| WO | WO 99/66979 | 12/1999 |
| WO | WO 00/03292 | 1/2000 |
| WO | WO 00/04838 | 2/2000 |
| WO | WO 00/04953 | 2/2000 |
| WO | WO 00/09212 | 2/2000 |
| WO | WO 00/29501 | 5/2000 |
| WO | WO 00/37137 | 6/2000 |
| WO | WO 00/45892 | 8/2000 |
| WO | WO 00/54836 | 9/2000 |
| WO | WO 00/57956 | 10/2000 |
| WO | WO 00/67845 | 11/2000 |
| WO | WO 00/78394 | 12/2000 |
| WO | WO 00/78395 | 12/2000 |

OTHER PUBLICATIONS

Lommatzsch et al., "Radiation effects on the optic nerve observed after brachytherapy of choroidal melanomas with 106Ru/106Rh plaques", *Graefe's Arch. Clin. Exp. Opthalmology* vol. 232, pp. 482–487, 1994.

*Radiotherapy of Intraoculare and Orbital Tumors*, Springer–Verlak publishers, Berlin Heidelberg and New York, copyright 1993, pp. 23–30 and 363–367.

Raloff, "Nuclear Medicine Gets Friendlier—Experimental Therapies Seek to Poison Just the Diease", *Science News*, Bol. 152, Jul. 19, 1997, pp. 40–41.

Sealy, R. et al., "The Treatment of Cancer of the Uvula and Soft Palate with Interstitial Radioactive Wire Implants," *Int. J. Radiation Oncology Biol. Phys.*, vol. 10, Oct. 1984, pp. 1951–1955.

Sinclair, W.K. et al. "Artificial Radioactive Sources for Interstitial Therapy," Source Unknown, Aug. 1952, pp. 417–419.

Wallace, D.M. et al., "Radioactive Tantalum Wire Implantation as a Method of Treatment for Early Carcinoma of the Bladder," Source Unknown, Aug. 1952, pp. 421–424.

Sutherland, "Managing Cancer Through Synergy", *Administrative Radiology Journal*, Nov. 1996, pp. 21–27.

Tjho–Heslinga et al., "Results of ruthenium irradiation of uveal melanoma", *Radiothereapy Oncology*, vol. 29, pp 33–38, 1993.

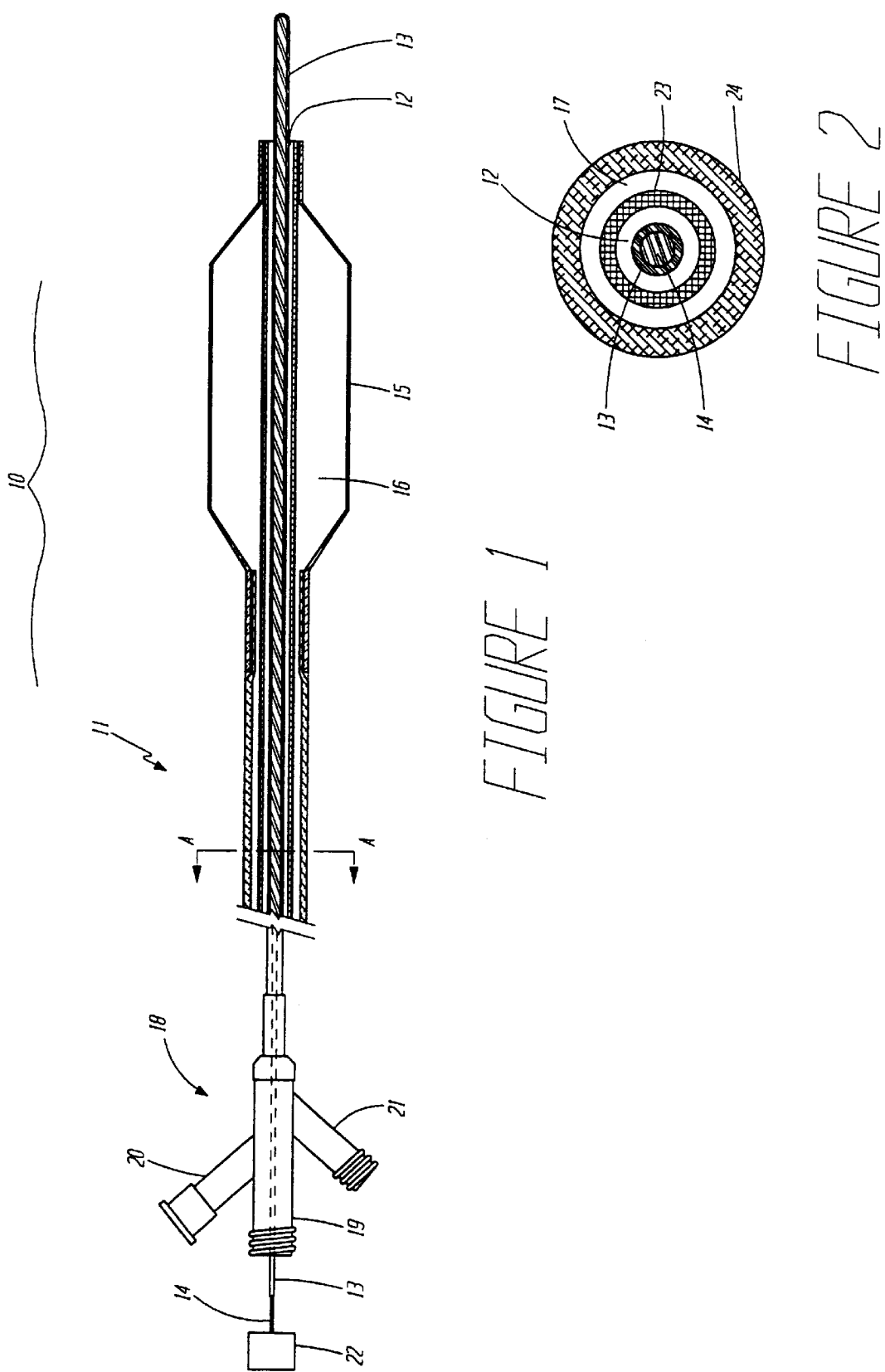

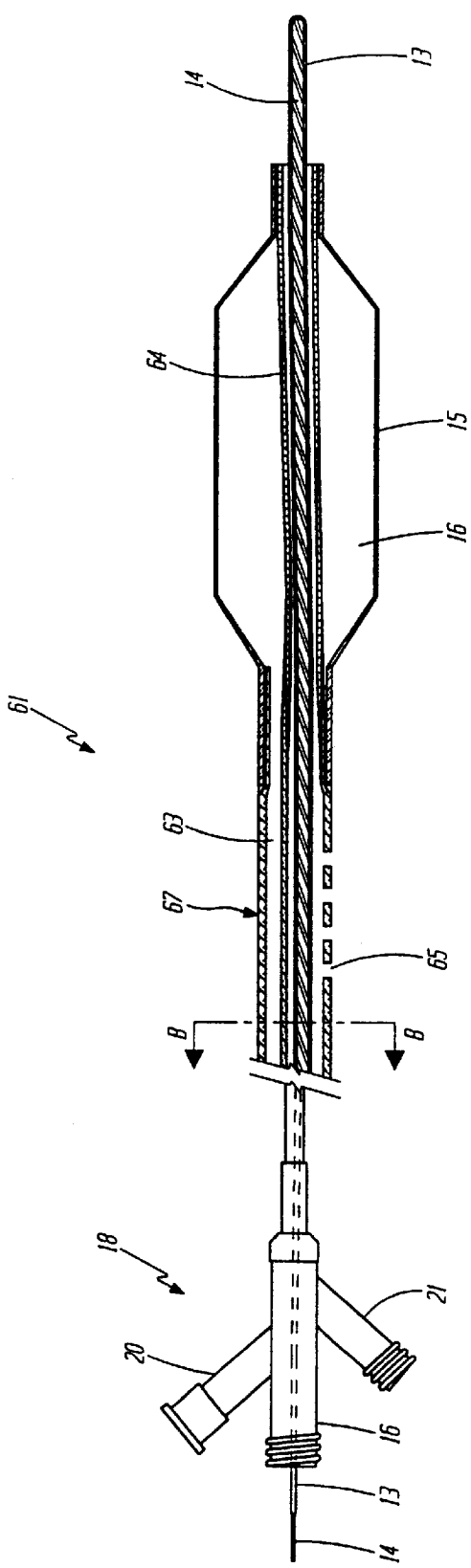
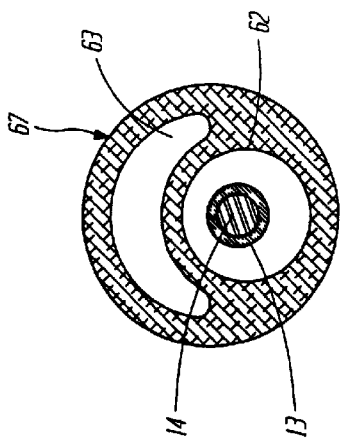
FIGURE 6
FIGURE 7

INTRAVASCULAR RADIATION DELIVERY SYSTEM

CROSS-REFERENCE TO RELATED APPLICATIONS

This application is a continuation of U.S. patent application Ser. No. 08/782,471 filed Jan. 10, 1997 now U.S. Pat. No. 6,234,951, which is a continuation-in-part of co-pending U.S. patent application Ser. No. 08/608,655 filed on Feb. 29, 1996 now U.S. Pat. No. 5,882,290 entitled INTRAVASCULAR RADIATION DELIVERY SYSTEM, the entire disclosure of which are incorporated herein by reference.

FIELD OF THE INVENTION

The present invention generally relates to intralumenal devices used to deliver radiation inside a living body. More specifically, the present invention relates to intravascular devices used to deliver radiation inside the vasculature of a patient for therapeutic purposes. Those skilled in the art will recognize the benefits of applying the present invention to similar fields not discussed herein.

BACKGROUND OF THE INVENTION

Intravascular diseases are commonly treated by relatively non-invasive techniques such as percutaneous translumenal angioplasty (PTA) and percutaneous translumenal coronary angioplasty (PTCA). These therapeutic techniques are well-known in the art and typically involve the use of a balloon catheter with a guide wire, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. For example, the restriction may redevelop over a period of time, a phenomenon commonly referred to as restenosis. Various theories have been developed to explain the cause for restenosis. It is commonly believed that restenosis is caused, at least in part, by cellular proliferation over a period of time to such a degree that a stenosis is reformed in the location of the previously dilated restriction.

Intravascular radiation, including thermal, light and radioactive radiation, has been proposed as a means to prevent or reduce the effects of restenosis. For example, U.S. Pat. No. 4,799,479 to Spears suggests that heating a dilated restriction may prevent gradual restenosis at the dilation site. In addition, U.S. Pat. No. 5,417,653 to Sahota et al. suggests that delivering relatively low energy light, following dilatation of a stenosis, may inhibit restenosis. Furthermore, U.S. Pat. No. 5,199,939 to Dake et al. suggests that intravascular delivery of radioactive radiation may be used to prevent restenosis. While most clinical studies suggest that thermal radiation and light radiation are not significantly effective in reducing restenosis, some clinical studies have indicated that intravascular delivery of radioactive radiation is a promising solution to the restenosis enigma.

Since radioactive radiation prevents restenosis but will not dilate a stenosis, radiation is preferably administered during or after dilatation. European Patent No. 0 688 580 to Verin discloses a device and method for simultaneously dilating a stenosis and delivering radioactive radiation. In particular, Verin '580 discloses balloon dilatation catheter having an open-ended lumen extending therethrough for the delivery of a radioactive guide wire.

One problem associated with the open-ended lumen design is that bodily fluids (e.g., blood) may come into contact with the radioactive guide wire. This may result in contamination of the bodily fluid and require the resterilization or disposal of the radioactive guide wire. To address these issues, U.S. Pat. No. 5,503,613 to Weinberger et al. proposes the use of a separate closed-ended lumen in a balloon catheter. The closed-ended lumen may be used to deliver a radioactive guide wire without the risk of contaminating the blood and without the need to resterilize or dispose of the radiation source.

The closed-ended lumen design also has draw backs. For example, the addition of a separate delivery lumen tends to increase the overall profile of the catheter. An increase in profile is not desirable because it may reduce flow rate of fluid injections into the guide catheter and it may interfere with navigation in small vessels.

Another problem with both the open-ended and closed-ended devices is that radiation must travel through the fluid filled balloon in order to reach the treatment site. While this is not a problem for gamma radiation, it poses a significant problem for beta radiation which does not penetrate as well as gamma radiation. Beta radiation is considered a good candidate for radiation treatment because it is easy to shield and control exposure. In larger vessels (e.g., 0.5 cm or larger), a fluid filled balloon absorbs a significant amount of beta radiation and severely limits exposure to the treatment site.

SUMMARY OF THE INVENTION

The present invention overcomes these problems by providing a radiation delivery system that permits the use of an open-ended delivery lumen without the risk of blood contamination and without the need to dispose of or resterilize the radiation source. In addition, the present invention provides a radiation delivery system that permits beta radiation to be delivered through a balloon without a significant decrease in radiation exposure to the treatment site, even in large vessels.

One embodiment of the present invention may be described as a catheter having an open-ended lumen, a radiation source disposed in the open-ended lumen of the catheter and a closed-end sheath surrounding the radiation source. The closed-end sheath prevents blood and other fluids from coming into contact with the radiation source so that blood is not contaminated and the radiation source may be reused. The catheter may be a balloon catheter and may include a guide wire disposed in the open-ended lumen of the catheter. The open-ended lumen may be a full-length lumen or a partial-length lumen (e.g., a rapid exchange lumen). Preferably, the lumen is centered in the balloon for uniform radiation delivery. The catheter may also include a blood perfusion lumen under the balloon or around the balloon. The open-ended lumen in the catheter may have a reduced diameter adjacent the distal end of the catheter to prevent the radiation source from exiting the lumen. Alternatively, the closed-end sheath may have a ridge which abuts a corresponding restriction in the open-end lumen of the catheter to prevent the radiation source from exiting the lumen.

Another embodiment of the present invention may be described as a method of delivering radiation to a treatment site inside the vasculature of a patient using a the radiation delivery system described above wherein the method includes the steps of (1) inserting the catheter into the vasculature of a patient; (2) inserting the radiation source into the closed-end sheath; (3) inserting the radiation source and the closed-end sheath into the lumen of the catheter such that the radioactive portion is positioned adjacent a treatment site; and (3) exposing the vascular wall to radiation from the radiation source. Alternatively, the sheath may be inserted into the catheter before the radiation source is loaded into the sheath. The method may also include the steps of (4) removing the radiation source from the catheter; and (5) removing the catheter from the patient. The catheter may be inserted into the vasculature over a guide wire and the guide wire may be removed from the catheter prior to exposing the vascular wall to radiation.

Yet another embodiment of the present invention may be described as a method of delivering radiation to a treatment site inside the vasculature of a patient using a gas-filled balloon catheter and a radiation source wherein the method includes the steps of: (1) inserting the catheter into the vasculature such that the balloon is adjacent to a treatment site; (2) inserting the radiation source into the catheter such that the radioactive portion is adjacent to the balloon; (3) inflating the balloon with a gas; and (4) exposing the treatment site to radiation from the radiation source through the gas in the balloon. The balloon may be inflated prior to or subsequent to inserting the radiation source. Preferably beta radiation is used, but other radioisotopes may be employed.

BRIEF DESCRIPTION OF THE DRAWINGS

FIG. 1 is a partially sectioned side view of an embodiment of the present invention.

FIG. 2 is a cross-sectional view taken at A—A in FIG. 1.

FIG. 6 is a partially sectioned side view of an alternative embodiment of the present invention including a perfusion lumen passing through the balloon.

FIG. 7 is a cross-sectional view taken at B—B in FIG. 6.

DETAILED DESCRIPTION OF THE INVENTION

Figure 3:
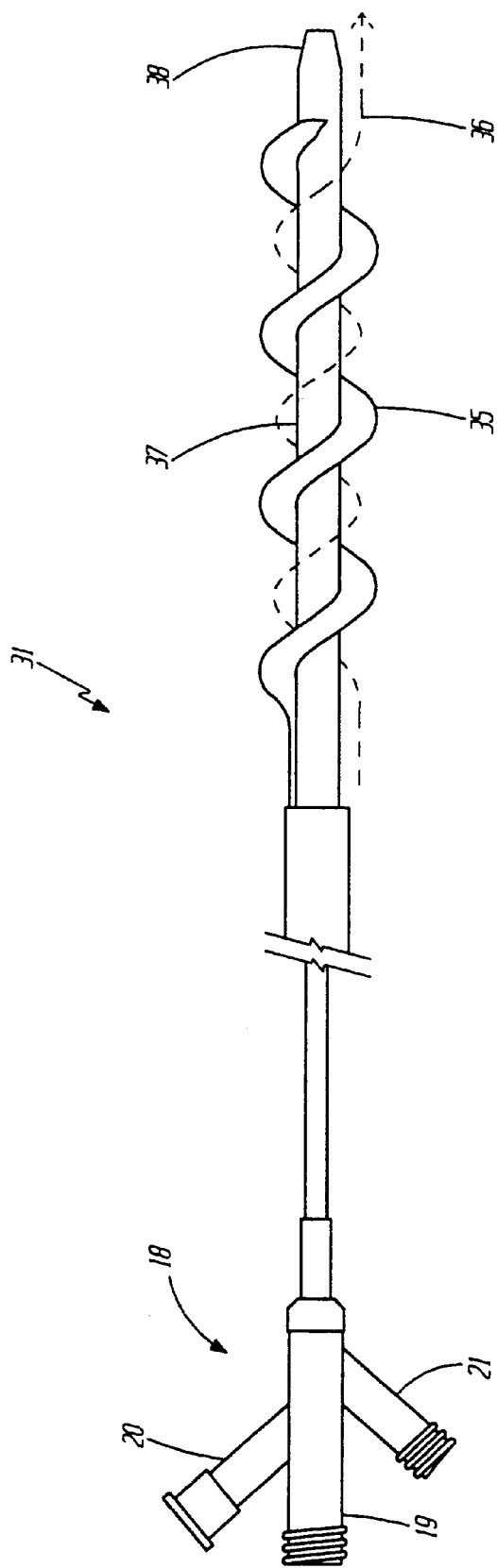
FIG. 3 is a side view of an alternative embodiment of the present invention including a helical-shaped balloon.

The following detailed description should be read with reference to the drawings in which similar parts in different drawings are numbered the same. The drawings, which are not necessarily to scale, depict exemplary embodiments and are not intended to limit the scope of the invention.

Examples of suitable materials, dimensions, parts, assemblies, manufacturing processes and methods of use are described for each embodiment. Otherwise, that which is conventional in the field of the invention may be implemented. Those skilled in the field will recognize that many of the examples provided have suitable alternatives which may also be utilized.

Refer now to FIGS. 1 and 2 which illustrate a radiation delivery system 10 of the present invention. Radiation delivery system 10 includes a catheter 11 having an open-ended lumen 12 extending therethrough. A closed-ended sheath 13 surrounds a radiation source 14 (such as a guide wire) disposed in the open-ended lumen 12. An after-loader 22 may be connected to the proximal end of the radiation source 14 to advance and retract the radiation source 14 and safely contain it when not in use.

The catheter 11 includes an inflatable balloon 15 having an interior 16 which is in fluid communication with an inflation lumen 17. The catheter 11 illustrated in FIGS. 1 and 2 has a coaxial shaft construction including an inner tube 23 and an outer tube 24. Other shaft constructions may be employed such as a dual lumen shaft design illustrated in FIG. 6. A manifold 18 is connected to the proximal end of the catheter 11 and includes a guide wire port 19 and a flush port 20 both of which are in fluid communication with the open-ended lumen 12. The guide wire port may include a toughy-borst (not shown) to seal about the proximal end of the closed-end sheath 13. The manifold 18 also includes an inflation port 21 which is in fluid communication with the inflation lumen 17 and the interior 16 of the balloon 15.

The closed-end sheath 13 preferably extends to the proximal end of the catheter 11 and may include means for connection to the after-loader 22. The closed-end sheath 13 may be formed of polyethylene, PTFE coated polyimide or other suitable flexible material. The closed-end sheath 13 may have a length of about 100 to 300 cm depending on the length of the catheter 11. A wall thickness between 0.0002 and 0.005 inches is preferred to minimize profile and radiation absorption.

As included with catheter 11 illustrated in FIGS. 1 and 2, the open-ended lumen 12, closed-ended sheath 13, radiation source 14, after loader 22 and toughy-borst are also included with catheters 31, 41, 51 and 61 as illustrated in FIGS. 3, 4, 5 and 6 respectively. In addition, those skilled in the art will appreciate that the various features of each catheter 11, 31, 41, 51 and 61 may be mixed and matched depending on the desired result. For example, the rapid exchange features of catheter 51 may be incorporated into perfusion catheter 61, resulting in a perfusion rapid exchange catheter for the delivery of radiation. As another example, the centering balloon 35 or 45 may be contained inside balloon 15 of catheters 11 and 61 to provide a centering function, even in curved vasculature.

Figure 4:
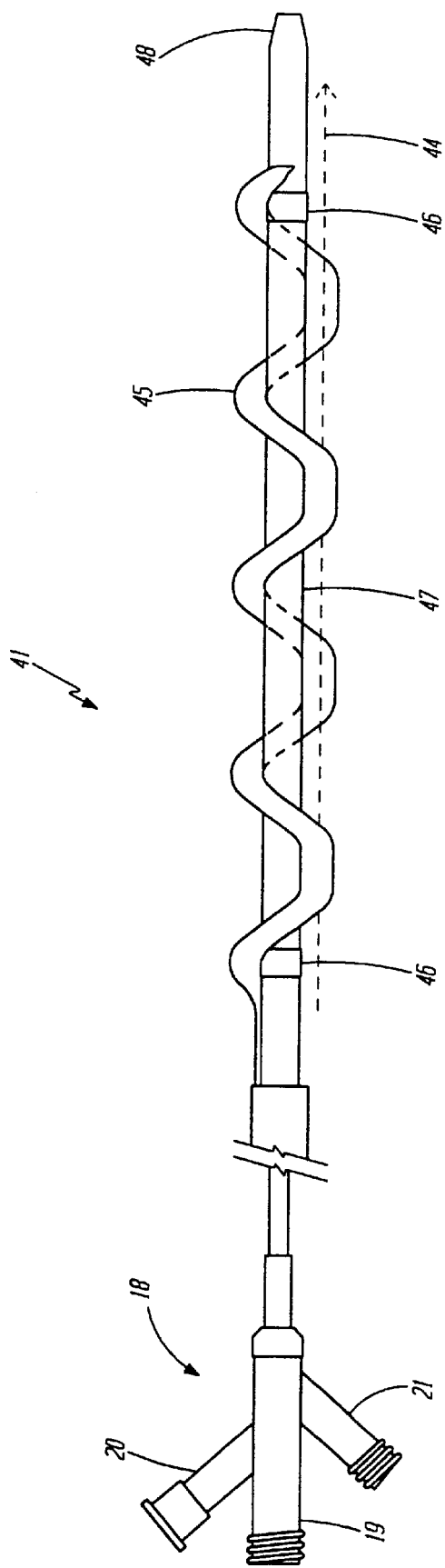
FIG. 4 is a side view of an alternative embodiment of the present invention including a toroidal-serpentine-shaped balloon.

Refer now to FIGS. 3 and 4 which illustrate alternative radiation delivery catheters 31 and 41. Alternative catheters 31 and 41 may be used in place of catheter 11 for the radiation delivery system 10 illustrated in FIG. 1. Except as described herein, the design and use of alternative catheters 31 and 41 is the same as catheter 11. Alternative catheter 41 may be made as described in co-pending U.S. patent application Ser. No. 08/608,655 which is incorporated herein by reference. Similarly, alternative catheter 31 may be made as described in the above-referenced case except that the balloon 35 is wound in a helical shape rather than a serpentine shape.

With reference to FIG. 3, alternative catheter 31 includes a helically-shaped balloon 35 which is wound around the distal end of the catheter 31. When the helically-shaped balloon 35 is inflated, a helically-shaped perfusion path 36 is defined between the balloon 35, the shaft 37 and the inside surface of the blood vessel. The blood perfusion path 36 allows blood to flow across the treatment site while the balloon 35 is inflated. In addition, the concentric and flexible helical shape of the inflated balloon 35 maintains the distal portion of the catheter 31 centered in the vessel, even around turns in the vasculature. Having the catheter 31 centered in a vessel permits the uniform distribution of radiation to the treatment site.

The distal end of the shaft 37 may include a reduced diameter tip 38 with a corresponding reduced inside diameter open-ended lumen (not visible). The reduced inside diameter permits a conventional guide wire to exit out the distal end of the catheter 31 but prohibits the sheath 13 and radioactive source wire 14 from exiting. This assumes, of course, that the sheath 13 or radioactive source wire 14 is larger than the guide wire. A reduced diameter tip may be included on any of the catheters described herein.

With reference to FIG. 4, alternative catheter 41 includes a toroidal-serpentine-shaped balloon 45. When the serpentine-shaped balloon 45 is inflated, a linear perfusion path 44 is defined between the balloon 45, the shaft 47 and the inside surface of the blood vessel. The blood perfusion path 44 allows blood to flow across the treatment site while the balloon 45 is inflated. As with the helical balloon described above, the concentric and flexible serpentine shape of the inflated balloon 45 maintains the distal portion of the catheter 41 centered in the vessel, even around turns in the vasculature. Having the catheter 41 centered in a vessel permits the uniform distribution of radiation to the treatment site. A further advantage of the serpentine-shaped balloon 45 is the relative linearity of the perfusion path 44 which tends to minimize resistance to blood flow.

Catheter 41 may also include two radiopaque markers 46 to facilitate radiographic placement in the vasculature. The distal end of the shaft 47 may include a reduced diameter tip 48 with a corresponding reduced inside diameter open-ended lumen (not visible). The reduced inside diameter permits a conventional guide wire to exit out the distal end of the catheter 41 but prohibits the sheath 13 and radioactive source wire 14 from exiting.

It is also contemplated that both the helical balloon 35 and the serpentine balloon 45 may be covered with an elastomeric sleeve to aid in collapsing the balloon 35/45 upon deflation. This sleeve would be connected to the shaft adjacent the proximal and distal ends of the balloon 35/45. It is further contemplated that this sleeve may include perfusion holes both proximally and distally to permit blood perfusion along the perfusion path 36/44 defined by the balloon 35/45. If a gas is used to inflate the balloon 35/45 in large diameter vessels (e.g., peripheral vasculature), it is preferred to not permit perfusion of blood which would otherwise absorb beta radiation. In such a situation, the sleeve would not include perfusion holes.

Figure 5A:
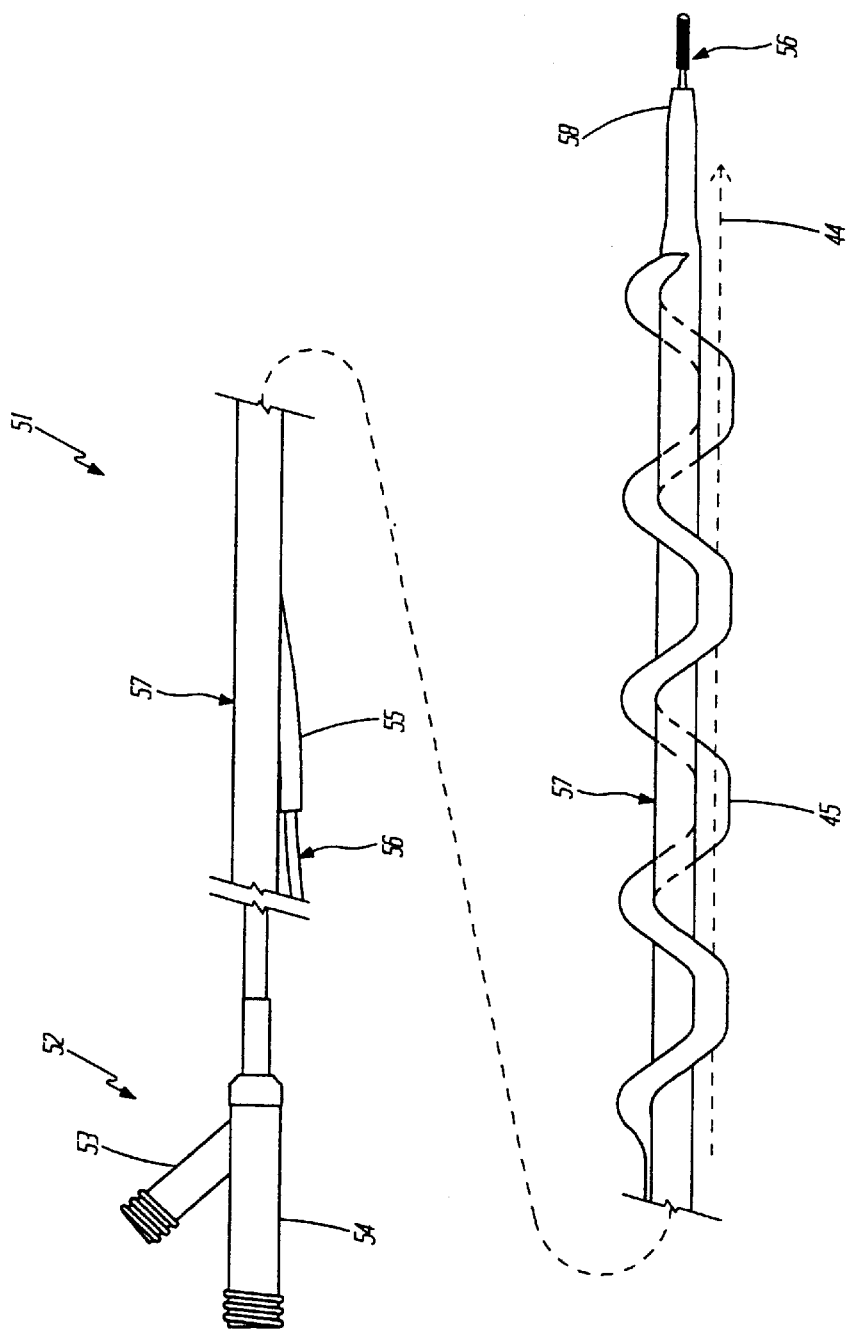
FIGS. 5a, 5b and 5c are partially sectioned side views of an alternative embodiment of the present invention including a rapid-exchange guide wire lumen.
Figure 5B:
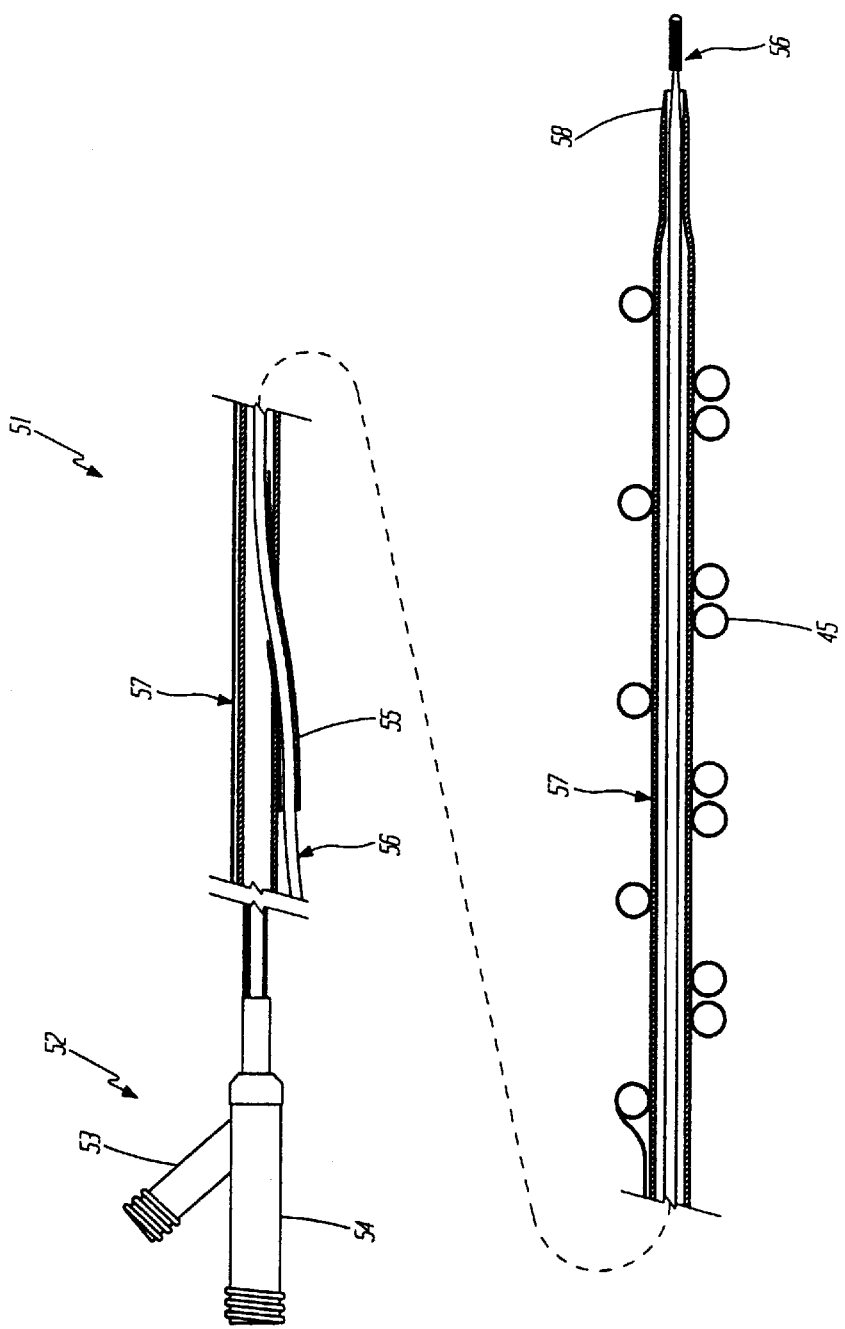
Figure 5C:
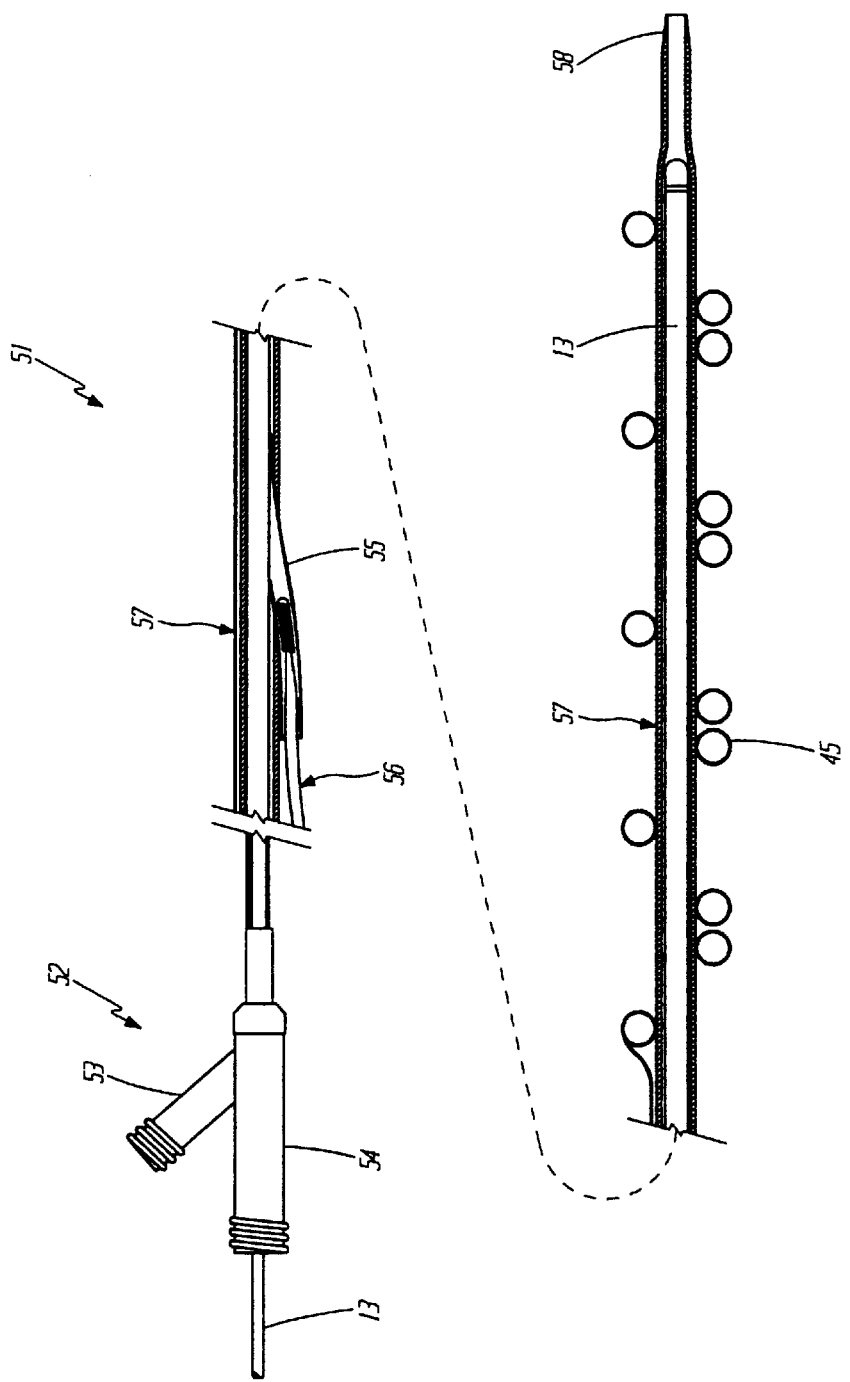

Refer now to FIGS. 5a, 5b and 5c which illustrate a rapid-exchange embodiment of the present invention. Alternative catheter 51 may be used in place of catheter 11 for the radiation delivery system 10 illustrated in FIG. 1. Except as described herein, the design and use of alternative catheter 51 is the same as catheter 11.

Rapid-exchange catheter 51 includes an elongate shaft 57 with a manifold 52 connected to the proximal end and a balloon 45 connected to the distal end. Although catheter 51 is shown with a serpentine balloon 45 and a corresponding linear perfusion path 44, any of the balloon types described herein may be used.

The manifold 52 includes a balloon inflation port 53 which is in fluid communication with the balloon 45 via a conventional inflation lumen. A radiation source entry port 54 is also included in the manifold 52. The entry port 54 communicates with the open-ended lumen and permits the insertion of the sheath 13 and radiation source 14. The open-ended lumen terminates in a reduced diameter tip 58 which permits a conventional guide wire 56 to exit out the distal end of the catheter 51 but prohibits the sheath 13 and radioactive source wire 14 from exiting.

The guide wire 56 enters the shaft 57 at the proximal guide wire tube 55. The guide wire tube 55 is located near the distal end of the catheter to permit catheter exchange without the need for an extension wire or wire trapping device. As best seen in FIG. 5c, the guide wire tube 55 has sufficient length such that the guide wire 56 may be pulled back and out of the open-ended lumen. In particular, the distance from the proximal end of the guide wire tube 55 to the distal end of the catheter 51 is less than the length of the guide wire extending outside of the patient's body. With the guide wire pulled back, the radioactive source wire 14 and the sheath 13 may be inserted into the entry port 54 to the distal end of the catheter 51.

Refer now to FIGS. 6 and 7 which illustrate an alternative perfusion catheter 61. Alternative catheter 61 may be used in place of catheter 11 for the radiation delivery system 10 illustrated in FIG. 1. Except as described herein, the design and use of alternative catheter 61 is the same as catheter 11.

Perfusion catheter 61 includes an elongate shaft 67 with a manifold 18 connected to the proximal end and a balloon 16 connected to the distal end. The shaft 67 is a multi-lumen type extrusion including an open-ended lumen 62 and an inflation lumen 63. Inflation lumen 63 provides fluid communication between the inflation port 21 and the interior of the balloon 16. Open ended lumen 62 is in communication with entry port 19 for the insertion of a guide wire (not shown) or the radioactive source 14 and sheath 13. A guide wire extension tube 64 is connected to the distal end of the multi-lumen shaft 67 and rigidly connects to the distal end of the balloon 15.

Catheter 61 includes a series of perfusion ports 65 which are in fluid communication with the distal portion of the open-ended lumen 62. The perfusion ports 65 permit blood to flow across the treatment site via the open-ended lumen while the balloon 15 is inflated.

Figure 8:
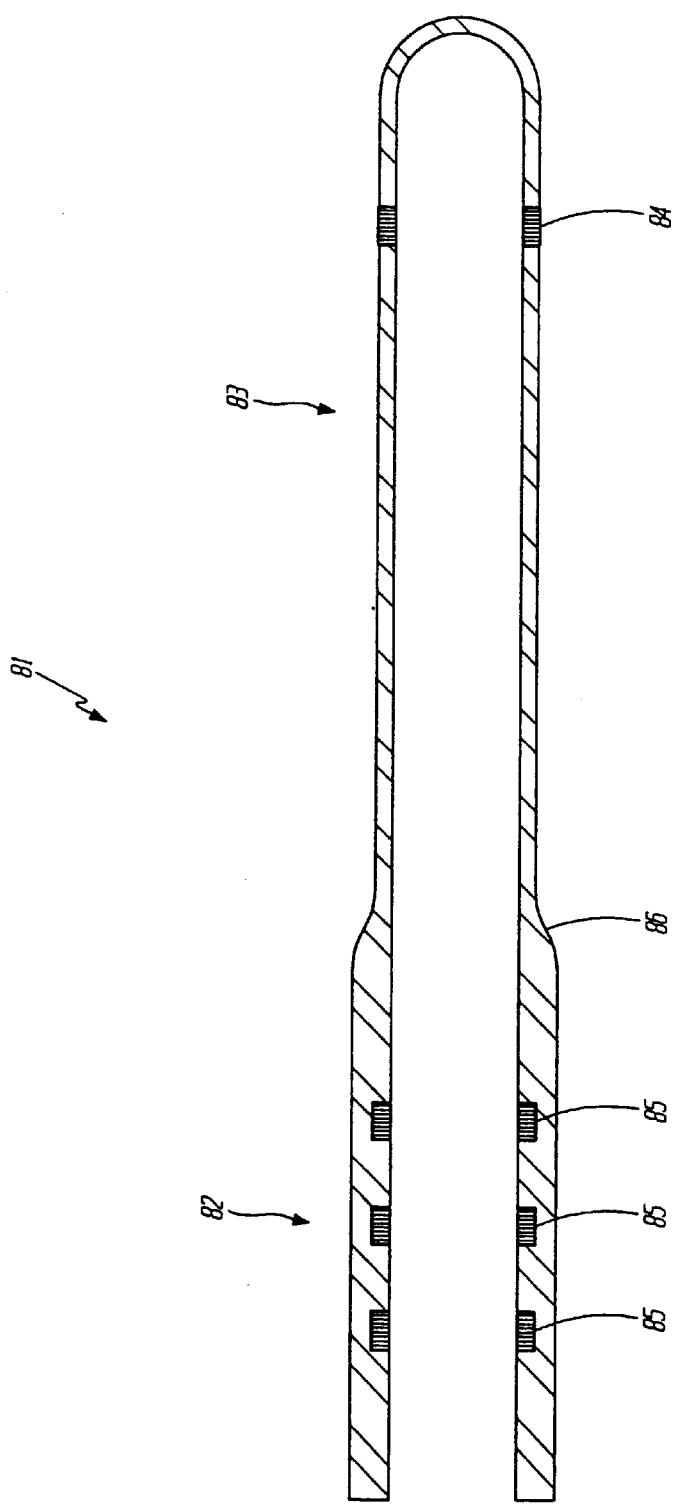
FIG. 8 is a cross-sectioned side view of an alternative sheath of the present invention.

With reference now to FIG. 8, an alternative sheath 81 is illustrated. Alternative sheath 81 may be used in place of sheath 13 for the radiation delivery system 10 illustrated in FIG. 1. Except as described herein, the design and use of alternative sheath 81 is the same as sheath 13.

Sheath 81 includes a proximal portion 82 and a distal portion 83, wherein the proximal portion 82 includes a relatively thicker wall and larger outside diameter. The thicker wall tends to absorb radiation to reduce the amount of unwanted exposure, particularly exposure of the medical personnel. The larger outside diameter of the proximal portion 84 may be used in conjunction with a corresponding restriction in the open-ended lumen 12 of any of the catheters described herein. Specifically, the leading edge or ridge 86 of the proximal portion 82 may abut a mating restriction in the open-ended lumen 12 such that the sheath 81 cannot be advanced beyond that point. The leading edge 86 and the mating restriction in the open-ended lumen serve the same function as the reduced diameter tip described previously and may be used in lieu thereof. In other words, the leading edge 86 and the mating restriction in the open-ended lumen would permit a conventional guide wire 56 to exit out the distal end of the catheter but would prohibit the sheath 81 and radioactive source wire 14 from exiting the distal end of the catheter.

The closed-end sheath 81 may include means for connection to the after-loader 22. The closed-end sheath 81 may be formed of polyethylene, PTFE coated polyimide or other suitable flexible material. The closed-end sheath 81 may have a length of about 100 to 300 cm depending on the length of the catheter 11. On the distal portion 83, a wall thickness between 0.0002 and 0.005 inches is preferred to minimize profile and radiation absorption. On the proximal portion 82, a wall thickness between 0.040 and 1.0 inches is preferred to maximize radiation absorption without significantly compromising profile. The outside diameter of the proximal portion 82 may be greater than the vascular access size on the portion of the sheath 81 that remains outside the body. Once the radiation source is inside the body, the risk of exposure of beta radiation to medical personnel in diminished.

Sheath 81 may also include a radiopaque marker 84 to facilitate radiographic placement of the sheath 81 and radioactive wire 14. Such a radiopaque marker 84 may also be included on sheath 13.

Sheath 81 may also include a series of annular magnets 85. Magnets 85 may be used to interact with a series of magnets connected to the catheter 11, 31, 41, 51 or 61 or a series of magnets connected to a guide catheter (not shown). This general arrangement is described in more detail in PCT publication WO 95/21566 which is fully incorporated herein by reference. The interacting magnets provide a means to longitudinally control and stabilize the position of the radiation source relative to the patient and treatment site.

In practice, catheters 11, 31, 41, 51 and 61 may be used to deliver radiation to the vascular wall in the following manner. After vascular access is established and a guide catheter is in position (if desired), the catheter 11/31/41/51/61 is inserted into the patient with the distal portion adjacent the treatment site. If a guide wire is used, the guide wire may be inserted prior to or simultaneously with the catheter. The balloon is then inflated to a low pressure sufficient to center the balloon in the vasculature and prevent movement of the catheter relative to the treatment site. Optionally, the balloon may first be inflated to a higher pressure in order to dilate the treatment site. If desired, the balloon may be inflated with a gas such as nitrogen, carbon dioxide or other non-toxic gas to minimize the absorption of radiation by the inflation media. After dilatation, the balloon is maintained in an inflated state, preferably at a low pressure, to center the catheter in the vascular lumen. The sheath 13 is placed over the radiation wire 14, preferably ahead of time, and the two are advanced into the open-ended lumen using an after-loader system. Optionally, the sheath 13 is first loaded into the open-ended lumen of the catheter and the proximal end of the sheath is connected to the after-loader, followed by insertion of the radioactive source wire 14. The toughy-borst is maintained sufficiently loose to allow advancement and may be locked to fully seal about the sheath 13 once the radiation wire 14 and sheath 13 are in the desired position. If a guide wire is used in the open-ended lumen, the guide wire is preferably retracted to permit passage of the radioactive wire 14 and sheath 13. If a rapid exchange catheter 51 is used, the guide wire is pulled back into the proximal guide wire tube 55. The vascular wall is then exposed to radiation (preferably beta radiation) for the desired period of time. The radioactive wire 14 and sheath 13 are removed from the catheter 11/31/41/51/61 and the catheter is removed from the patient.

While the specification describes the preferred embodiments, those skilled in the art will appreciate the spirit and scope of the invention with reference to the appended claims. Claims directed to methods of the present invention may be read without regard as to the order of the steps unless contraindicated by the teachings herein.

What is claimed is:

1. An intravascular catheter system, comprising:
   an elongate catheter including a distally disposed balloon, a radiation source lumen having an open distal end and a perfusion path, the balloon having a non-linear shape and the perfusion path having a linear shape; and
   an elongate radiation source disposed in the radiation source lumen.

2. An intravascular catheter system as in claim 1, wherein the perfusion path is defined in part by the balloon.

3. An intravascular catheter system as in claim 1, wherein the balloon is gas-filled.

4. An intravascular catheter system as in claim 1, wherein the elongate radiation source is disposed in a sheath.

5. An intravascular catheter system as in claim wherein the sheath has a closed distal end.

6. An intravascular catheter system as in claim 5, wherein the sheath has a wall thickness of between 0.0002 inches and 0.005 inches.

7. An intravascular catheter system, comprising:
   an elongate catheter including a distally disposed balloon, a radiation source lumen, the balloon having a non-linear shape; and
   an elongate sheath disposed in the radiation source lumen, the sheath having a wall thickness of between 0.0002 inches and 0.005 inches; and
   an elongate radiation source disposed in the sheath.

8. An intravascular catheter system as in claim 7, wherein the sheath has a closed distal end.

9. An intravascular catheter system as in claim 8, wherein the radiation source lumen has an open distal end.

10. An intravascular catheter system as in claim 7, wherein the catheter includes a perfusion path.

11. An intravascular catheter system as in claim 10, wherein the perfusion path has a linear shape.

12. An intravascular catheter system as in claim 11, wherein the perfusion path is defined in part by the balloon.

13. An intravascular catheter system as in claim 7, wherein the balloon is gas-filled.

14. The intravascular catheter of claim 1, wherein the perfusion path is thin the radiation source lumen.

15. The intravascular catheter of claim 10, wherein the perfusion path is within the radiation source lumen.

* * * * *

UNITED STATES PATENT AND TRADEMARK OFFICE
CERTIFICATE OF CORRECTION

PATENT NO. : 6,599,230 B2
DATED : July 29, 2003
INVENTOR(S) : R.N. Hastings et al.

It is certified that error appears in the above-identified patent and that said Letters Patent is hereby corrected as shown below:

Title page,
Item [56], References Cited, U.S. PATENT DOCUMENTS, insert in appropriate order:
-- 6,090,035   7/2000   Campbell et al.
   6,099,455   8/2000   Columbo et al.
   6,106,454   8/2000   Berg et al.
   6,110,097   8/2000   Hastings et al.
   6,117,065   9/2000   Hastings et al.
   6,142,926   11/2000   Schneiderman
   6,146,322   11/2000   Papirov et al.
   6,149,574   11/2000   Trauthen et al.
   6,149,575   11/2000   Leonhardt
   6,152,869   11/2000   Park et al.
   6,162,165   12/2000   Apple et al.
   6,179,768   1/2001   Loffler et al.
   6,200,256   3/2001   Weinberger
   6,200,257   3/2001   Winkler
   6,200,307   3/2001   Kasinkas et al.
   6,203,485   3/2001   Urick
   6,213,976   4/2001   Trerotola
   6,217,503   4/2001   Weinberger et al.
   6,224,535   5/2001   Chiu et al.
   6,224,536   5/2001   Pike
   6,231,495   5/2001   Denk
   6,231,719   5/2001   Garvey et al.
   6,234,952   5/2001   Lipric
   6,238,332   5/2001   Kanesaka
   6,241,719   6/2001   Wallace et al.
   6,248,057   6/2001   Mavity et al.
   6,251,059   6/2001   Apple et al.
   6,254,552   7/2001   Lewis et al.
   6,258,019   7/2001   Verin et al.
   6,261,219   7/2001   Meloul et al.
   6,264,579   7/2001   Odai et al.
   6,264,595   7/2001   Delfino et al.
   6,264,596   7/2001   Weadock
   6,264,598   7/2001   Armini
   6,267,717   7/2001   Stoll et al.
   6,267,775   7/2001   Clerc et al.
   6,283,910   9/2001   Bradshaw et al.
   6,283,911   9/2001   Keren --

UNITED STATES PATENT AND TRADEMARK OFFICE
CERTIFICATE OF CORRECTION

PATENT NO.    : 6,599,230 B2
DATED         : July 29, 2003
INVENTOR(S)   : R.N. Hastings et al.

It is certified that error appears in the above-identified patent and that said Letters Patent is hereby corrected as shown below:

Title page (cont's),
Item [56], References Cited, FOREIGN PATENT DOCUMENTS, insert in appropriate order :
-- WO      WO 01/60443 A1  8/2001
   WO      WO 01/54764 A2  8/2001
   WO      WO 01/47602 A1  7/2001
   WO      WO 01/26734 A1  4/2001
   WO      WO 01/21248 A1  3/2001
   WO      WO 01/21245 A1  3/2001
   WO      WO 01/21106 A1  3/2001
   WO      WO 01/14617 A1  3/2001
   WO      WO 01/14011 A1  3/2001
   WO      WO 00/76557     12/2000
   WO      WO 00/74778     12/2000
   WO      WO 00/69503     11/2000
   WO      WO 00/56249     9/2000
   WO      WO 00/45627     8/2000
   WO      WO 00/32271     6/2000
   JP      2000024001      1/2000 --; and
OTHER PUBLICATIONS, "Raloff" reference, " "*Diease*"," should read -- *Disease*", --

Column 8,
Line 27, "as in claim wherein" should read -- as in claim 4, wherein --
Line 54, "thin" should read -- within --

Signed and Sealed this

Third Day of August, 2004

JON W. DUDAS
*Acting Director of the United States Patent and Trademark Office*